US009115105B2

(12) United States Patent
Nair et al.

(10) Patent No.: US 9,115,105 B2
(45) Date of Patent: Aug. 25, 2015

(54) PRODUCTION OF PROPYLENE OXIDE

(75) Inventors: Hari Nair, Houston, TX (US); Charles Morris Smith, Princeton, NJ (US); James R. Lattner, LaPorte, TX (US); Krystle J. Chavez, Houston, TX (US); James C. Vartuli, Bradenton, FL (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/348,414

(22) PCT Filed: Aug. 30, 2012

(86) PCT No.: PCT/US2012/053184
§ 371 (c)(1),
(2), (4) Date: Jul. 11, 2014

(87) PCT Pub. No.: WO2013/058877
PCT Pub. Date: Apr. 25, 2013

(65) Prior Publication Data
US 2015/0126756 A1  May 7, 2015

Related U.S. Application Data

(60) Provisional application No. 61/548,384, filed on Oct. 18, 2011.

(51) Int. Cl.
| | | |
|---|---|---|
| *C07D 301/03* | (2006.01) | |
| *C07C 37/08* | (2006.01) | |
| *C07D 301/19* | (2006.01) | |
| *C09K 11/61* | (2006.01) | |
| *C09K 11/77* | (2006.01) | |
| *H01J 61/44* | (2006.01) | |
| *H01L 33/50* | (2010.01) | |
| *C07C 1/24* | (2006.01) | |
| *C07C 5/03* | (2006.01) | |
| *C07C 29/132* | (2006.01) | |
| *C07C 407/00* | (2006.01) | |

(52) U.S. Cl.
CPC ............... *C07D 301/19* (2013.01); *C07C 1/24* (2013.01); *C07C 5/03* (2013.01); *C07C 29/132* (2013.01); *C07C 407/00* (2013.01); *C09K 11/617* (2013.01); *C09K 11/7721* (2013.01); *C09K 11/7734* (2013.01); *C09K 11/7774* (2013.01); *C09K 11/7792* (2013.01); *H01J 61/44* (2013.01); *H01L 33/502* (2013.01); *C07C 2101/14* (2013.01)

(58) Field of Classification Search
CPC ............ C07C 37/08; C07C 1/24; C07C 5/03; C07C 29/132; C07C 407/00; C07C 2101/14; C07D 301/10; C07D 301/12; C07D 301/19; C09K 11/617; C09K 11/7721; C09K 11/7734; C09K 11/7774; C09K 11/7792; H01J 61/44; H01L 33/502
USPC .......................................... 549/523; 568/798
See application file for complete search history.

(56) References Cited

U.S. PATENT DOCUMENTS

| | | | |
|---|---|---|---|
| 6,984,761 B2 | 1/2006 | Levin et al. | |
| 2011/0105805 A1* | 5/2011 | Buchanan et al. | 568/798 |

FOREIGN PATENT DOCUMENTS

| | | |
|---|---|---|
| WO | WO 2004/058672 | 7/2004 |
| WO | WO 2005/093010 | 10/2005 |
| WO | WO 2010/024975 | 3/2010 |

OTHER PUBLICATIONS

Bobylev et al , Simultaneous preparation of ethylene oxide and propylene oxide by the hydroperoxide epoxidation of olefins, 1976, Neftekhimiya, 16 (2), p. 255-261 (abstract page).*
Bobylev et al., "Simultaneous Preparation of Ethylene Oxide and Propylene Oxide by the Hydroperoxide Epoxidation of Olefins". Chemical Abstracts Service, STN, Database accession No. 1976: 462877; Neftckhimiya, 16(2), pp. 255-261, 1976.

* cited by examiner

*Primary Examiner* — T. Victor Oh
(74) *Attorney, Agent, or Firm* — Siwen Chen; Stephen A. Baehl

(57) ABSTRACT

In a process for producing propylene oxide, cyclohexylbenzene is contacted with an oxygen-containing compound under oxidation conditions with or without a suitable catalyst to produce an oxidation reaction effluent comprising cyclohexylbenzene hydroperoxide. At least a portion of the cyclohexylbenzene hydroperoxide is then reacted with propylene in the presence of an epoxidation catalyst under conditions effective to produce an epoxidation reaction effluent comprising phenylcyclohexanol and propylene oxide.

20 Claims, No Drawings

PRODUCTION OF PROPYLENE OXIDE

PRIORITY CLAIM TO RELATED APPLICATIONS

This application is a National Stage Application of International Application No. PCT/US2012/053184 filed Aug. 30, 2012, which claims priority to U.S. Provisional Application Serial No. 61/548,384 filed Oct. 18, 2011, the disclosures of which are fully incorporated herein by their reference.

FIELD

The present invention relates to a process for producing propylene oxide, optionally in combination with phenol.

BACKGROUND

Propylene oxide is used in the production of polyether polyols, which are precursors in the manufacture of polyurethane resins, and in the production of propylene glycol.

The traditional route for the production of propylene oxide proceeds via the conversion of propylene to chloropropanols, which then undergo dehydrochlorination to the desired oxide. More recently, interest has focused on oxidation methods, for example the direct oxidation of propylene with hydrogen peroxide or the co-oxidation of propylene with isobutene, ethylbenzene, or cumene.

U.S. Pat. No. 6,984,761 discloses a process for co-producing propylene oxide and α-methyl styrene along with phenol and acetone by oxidizing cumene to cumene hydroperoxide and then reacting part of the cumene hydroperoxide with propylene in the presence of an epoxidation catalyst to form propylene oxide and dimethyl phenyl carbinol. The propylene oxide is separated from the reaction stream leaving a stream containing dimethyl phenyl carbinol. The dimethyl phenyl carbinol-containing stream and the remaining portion of the cumene hydroperoxide stream are converted in the presence of a catalyst, preferably an acidic catalyst, to form a product stream containing phenol, acetone, and α-methyl styrene.

The process of '761 patent allegedly has the advantage that, by controlling the fraction of the cumene hydroperoxide converted to dimethyl phenyl carbinol, the amount of α-methyl styrene produced can be continuously set to meet the market demand for α-methyl styrene. However, the world demand for α-methyl styrene is limited. Moreover, the market for phenol is growing more rapidly than that for the acetone co-product.

According to the invention, it has now been found that propylene oxide can be produced by reaction of propylene with cyclohexylbenzene hydroperoxide in the presence of an epoxidation catalyst. This process has the advantage that its co-product is phenylcyclohexanol, which can readily be converted to cyclohexylbenzene by dehydration to phenylcyclohexene followed by hydrogenation of the phenylcyclohexene. The cyclohexylbenzene can then be recycled back to the oxidation step used to produce the cyclohexylbenzene hydroperoxide. Moreover, by supplying part of the cyclohexylbenzene hydroperoxide to a cleavage reaction, it is possible to co-produce phenol/cyclohexanone with the propylene oxide. Not only is cyclohexanone of more value than the α-methyl styrene co-product of the '761 patent but, if desired, part or all of the cyclohexanone can be dehydrogenated to produce additional phenol. Moreover, the ratio of propylene oxide to phenol/cyclohexanone can be readily adjusted according to their relative market demands.

SUMMARY

In one aspect, the invention relates to a process for producing propylene oxide, the process comprising:

(a) contacting a composition comprising at least 0.5 wt % cyclohexylbenzene based upon the total weight of the composition with an oxygen-containing compound under oxidation conditions to produce an oxidation reaction effluent comprising at least 0.5 wt % cyclohexylbenzene hydroperoxide based upon the total weight of the oxidation reaction effluent; and (b) reacting at least a portion of the cyclohexylbenzene hydroperoxide produced in (a) with propylene in the presence of an epoxidation catalyst under conditions effective to produce an epoxidation reaction effluent comprising phenylcyclohexanol and propylene oxide.

Conveniently, the contacting (a) is conducted in the presence of an oxidation catalyst comprising a cyclic imide, such as N-hydroxyphthalimide.

Conveniently, the epoxidation catalyst comprises a metal and a support. The metal is generally selected from one or more of a Group 1 metal, a Group 2 metal, a Group 3 metal, a Group 8 transition metal, a Group 9 transition metal, a Group 10 transition metal, and mixtures thereof, whereas the support is generally selected from one or more of silica, alumina, crystalline or amorphous aluminophosphates, Group 4 metal oxides, mesoporous molecular sieves, and mixtures thereof.

In one embodiment, the epoxidation catalyst comprises cobalt on a support comprising zirconium oxide, an aluminophosphate or a mixture thereof.

Conveniently, the process further comprises:

(c) separating at least a portion of the propylene oxide from the epoxidation reaction effluent to leave a phenylcyclohexanol-containing stream;

(d) dehydrating at least a portion of the phenylcyclohexanol in said phenylcyclohexanol-containing stream to phenylcyclohexene;

(e) hydrogenating at least a portion of the phenylcyclohexene from (d) to cyclohexylbenzene; and (f) recycling the cyclohexylbenzene from (e) to said contacting (a).

In a further aspect, the invention relates to a process for co-producing phenol and propylene oxide, the process comprising:

(a) contacting cyclohexylbenzene with an oxygen-containing compound under oxidation conditions effective to produce an oxidation reaction effluent comprising cyclohexylbenzene hydroperoxide;

(b) reacting a first part of the cyclohexylbenzene hydroperoxide produced in (a) with propylene in the presence of an epoxidation catalyst under conditions effective to produce an epoxidation reaction effluent comprising phenylcyclohexanol and propylene oxide; and (c) contacting a second part of the cyclohexylbenzene hydroperoxide produced in (a) with a cleavage catalyst under conditions effective to convert said cyclohexylbenzene hydroperoxide into phenol and cyclohexanone.

Conveniently, the cleavage catalyst is an acid catalyst, such as sulfuric acid, an aluminosilicate zeolite, or a mixed metal oxide.

In yet a further aspect, the invention relates to a process for co-producing phenol and propylene oxide, the process comprising:

(a) contacting benzene with hydrogen in the presence of a hydroalkylation catalyst under conditions effective to produce cyclohexylbenzene;

(b) contacting cyclohexylbenzene from (a) with an oxygen-containing compound under oxidation conditions effective to produce an oxidation reaction effluent comprising cyclohexylbenzene hydroperoxide;

(c) reacting a first part of the cyclohexylbenzene hydroperoxide produced in (b) with propylene in the presence of an epoxidation catalyst under conditions effective to produce an epoxidation reaction effluent comprising phenylcyclohexanol and propylene oxide;

(d) contacting a second part of the cyclohexylbenzene hydroperoxide produced in (b) with a cleavage catalyst under conditions effective to convert said cyclohexylbenzene hydroperoxide into phenol and cyclohexanone;

(e) separating at least a portion of the propylene oxide from the epoxidation reaction effluent to leave a phenylcyclohexanol-containing stream;

(f) dehydrating at least a portion of the phenylcyclohexanol in said phenylcyclohexanol-containing stream to phenylcyclohexene;

(g) hydrogenating at least a portion of the phenylcyclohexene from (f) to cyclohexylbenzene; and (h) recycling at least a portion of the cyclohexylbenzene from (g) to said contacting (a).

DETAILED DESCRIPTION

Described herein is a process for producing propylene oxide, optionally in combination with phenol, or phenol and cyclohexanone. In the present process cyclohexylbenzene is contacted with an oxygen-containing compound, optionally in the presence of an oxidation catalyst, to produce an oxidation reaction effluent comprising cyclohexylbenzene hydroperoxide. At least a portion of the cyclohexylbenzene hydroperoxide is then reacted with propylene in the presence of an epoxidation catalyst to produce phenylcyclohexanol and propylene oxide. The propylene oxide is recovered as a process product, whereas the phenylcyclohexanol is generally converted back to cyclohexylbenzene by dehydration and hydrogenation.

Where it is desired to produce phenol or phenol and cyclohexanone in addition to propylene oxide, a further part of the cyclohexylbenzene hydroperoxide is contacted with a cleavage catalyst to convert the cyclohexylbenzene hydroperoxide into phenol and cyclohexanone. The cyclohexanone can be recovered as a sellable product or can be dehydrogenated to produce additional phenol.

In one preferred embodiment, the present process forms part of an integrated process for co-producing phenol and propylene oxide from benzene and propylene. In this process, the benzene is converted to cyclohexylbenzene, which is then oxidized to cyclohexylbenzene hydroperoxide and a portion of the cyclohexylbenzene hydroperoxide is cleaved to produce phenol and cyclohexanone and a portion of the cyclohexylbenzene hydroperoxide is reacted with propylene to produce propylene oxide. The present process will therefore now be more particularly described with reference to this preferred embodiment.

Production of the Cyclohexylbenzene

In one step of the integrated process, cyclohexylbenzene is produced by reacting the benzene with cyclohexene in the presence of a catalyst having an alkylation function and under conditions to promote the following reaction:

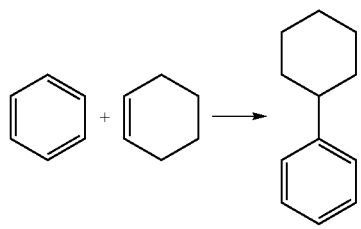

The cyclohexene can be supplied to the reaction zone as a separate feed from the benzene, but normally is produced in situ by selective hydrogenation of the benzene in the presence of a hydrogenation component provided on the catalyst having the alkylation function. The bifunctional catalyst is therefore referred to herein as a hydroalkylation catalyst and, overall, the hydroalkylation reaction proceeds as follows to produce cyclohexylbenzene (CHB):

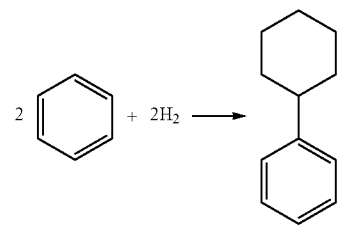

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4:1 and about 0.9:1.

In various embodiments, the composition produced in the hydroalkylation step contains at least 0.5 wt %, or at least 1 wt %, or at least 5 wt %, or at least 10 wt %, or at least 30 wt %, or at least 50 wt % of cyclohexylbenzene, based upon the total weight of the composition.

In addition to the benzene and hydrogen, a diluent, which is substantially inert under hydroalkylation conditions, may be supplied to the hydroalkylation reaction. Typically the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference;)

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from, but composited with, the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification. Suitable metal oxide binders include silica, alumina, zirconia, titania, silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

Although the hydroalkylation reaction using an MCM-22 family zeolite catalyst activated by the process described herein is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 hr$^{-1}$ to about 10 hr$^{-1}$ on total feed, and a benzene/dicyclohexylbenzene weight ratio about of 1:1 to about 5:1.

Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as WO$_x$/ZrO$_2$, phosphoric acid, sulfated zirconia, and mixtures thereof. Generally, the acid catalyst includes at least one aluminosilicate, aluminophosphate, or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a C$_6$-rich stream comprising cyclohexane and unreacted benzene can be readily removed from the hydroalkylation reaction effluent by distillation, owing to the similarity in the boiling points of benzene and cyclohexane, the C$_6$-rich stream is difficult to further separate by simple distillation. However, some or all of the C$_6$-rich stream can be recycled to the hydroalkylation reactor to provide not only part of the benzene feed but also part of the diluents mentioned above.

In some cases, it may be desirable to supply some of the C$_6$-rich stream to a dehydrogenation reaction zone, where the C$_6$-rich stream is contacted with a dehydrogenation catalyst under dehydrogenation conditions sufficient to convert at least part of the cyclohexane in the C$_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from one or more of, or the group consisting of, silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Typically, the hydrogenation-dehydrogenation component is present in an amount between about 0.1 wt % and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 wt % and about 5 wt % of the catalyst. Suitable dehydrogenation conditions include a temperature of about 250° C. to about 550° C., a pressure of about atmospheric to about 500 psig (100 kPa to 3550 kPa), a weight hourly space velocity of about 0.2 hr$^{-1}$ to 50 hr$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the C$_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

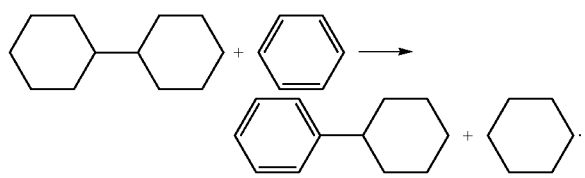

The catalytic treatment can be conducted on the direct product of the hydroalkylation reaction or after distillation of the hydroalkylation reaction product to separate the C$_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Cyclohexylbenzene Oxidation

In order to convert the cyclohexylbenzene into phenol and propylene oxide, the cyclohexylbenzene may be oxidized to the corresponding hydroperoxide. This is accomplished by contacting the cyclohexylbenzene with an oxygen-containing compound, such as air and various derivatives of air. For example, it is possible to use air that has been compressed and filtered to remove particulates, air that has been compressed and cooled to condense and remove water, or air that has been enriched in oxygen above the natural approximately 21 mol % in air through membrane enrichment of air, cryogenic separation of air, or other conventional means.

The oxidation can be conducted in the presence of a cyclic imide catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo [2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 wt % to 5 wt %, of the cyclohexylbenzene.

Suitable conditions for the oxidation step (i.e., oxidation conditions) include a temperature between about 70° C. and about 200° C., such as about 90° C. to about 130° C., and a pressure of about 50 kPa to 10,000 kPa. Lower temperatures (50° C.-100° C.) may be used if no oxidation catalyst is used. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaceously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 0.5 wt %, or at least 1 wt %, such as at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent may be subjected to a cleavage reaction, with or without undergoing any prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3A molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Publication No. WO 2009/025939.

Hydroperoxide Cleavage

In various embodiments, all or a portion of the cyclohexyl-1-phenyl-1-hydroperoxide produced in the oxidation step is converted into phenol and cyclohexanone by an acid-catalyzed cleavage step.

Generally, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm to no greater than 3000 wppm, or at least 150 wppm to no greater than 2000 wppm of the acid catalyst, or at least 300 wppm and no greater than 1500 wppm of the acid catalyst, based upon total weight of the cleavage reaction mixture.

In other embodiments, a heterogeneous acid catalyst is employed for the cleavage reaction, such as molecular sieve, and in particular a molecular sieve having a pore size in excess of 7 Å. Examples of suitable molecular sieves include zeolite beta, zeolite Y, zeolite X, ZSM-12, and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

Generally, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major products of the cleavage reaction of cyclohexyl-1-phenyl-1-hydroperoxide are phenol and cyclohexanone, which are present in substantially equimolar proportions and can be recovered from the cleavage effluent by any known method. Depending on market conditions, part or all of the cyclohexanone can be dehydrogenated to produce additional phenol by, for example, the process disclosed in U.S. Published Patent Application No. 2011/0105805.

Uses of Cyclohexanone and Phenol

The cyclohexanone produced through the processes disclosed herein may be used, for example, as an industrial solvent, as an activator in oxidation reactions, and in the production of adipic acid, cyclohexanone resins, cyclohexanone oxime, caprolactam, and nylons, such as nylon 6 and nylon 6,6.

The phenol produced through the processes disclosed herein may be used, for example, to produce phenolic resins, bisphenol A, $\epsilon$-caprolactam, adipic acid, and/or plasticizers.

Production of Propylene Oxide

In various embodiments, all or a portion of the cyclohexylbenzene hydroperoxide (e.g., cyclohexyl-1-phenyl-1-hydroperoxide) produced in the oxidation step is converted into propylene oxide by reaction with propylene in the presence of an epoxidation catalyst. In various embodiments, at least 1 wt %, or at least 5 wt %, or at least 10 wt % of the cyclohexyl-1-phenyl-1-hydroperoxide from the product of the oxidation step discussed above is converted into propylene oxide.

The epoxidation catalyst may be any material that is suitable to cause an epoxidation reaction. A suitable epoxidation catalyst comprises a metal or metal compound on a support. Generally, the metal is selected from one or more of, or the group consisting of, a Group 1 metal, a Group 2 metal, a Group 3 metal, a Group 8 transition metal, a Group 9 transition metal, a Group 10 transition metal, and mixtures thereof and may be present in any amount suitable to effect an epoxidation reaction. Suitable supports include silica, alumina, crystalline or amorphous aluminophosphates, Group 4 metal oxides, mesoporous molecular sieves, and mixtures thereof. In one preferred embodiment, the epoxidation catalyst comprises cobalt on a support comprising zirconium oxide, an aluminophosphate, or a mixture thereof.

The epoxidation reaction is typically conducted under conditions including a temperature of about 20° C. to about 200° C., such as 40° C. to about 120° C. and a pressure of about 100 kPa to about 2000 kPa, such as 100 kPa to about 1000 kPa with the molar ratio of cyclohexylbenzene hydroperoxide to propylene generally varying between 1:100 and 100:1. Conditions can be changed to obtain desired conversions and yields of propylene oxide.

The epoxidation reaction produces propylene oxide, which can be separated from the other constituents of the product stream using a suitable separation scheme, preferably distillation, to form a phenylcyclohexanol-containing stream, which may comprise any amount of phenylcyclohexanol.

Similarly, excess unreacted propylene may be removed from the product stream, either in conjunction with, or separately from the propylene oxide. In certain embodiments, the remainder of the product stream (e.g., phenylcyclohexanol-containing stream) is primarily composed of phenyl cyclohexanol and cyclohexylbenzene. All or a portion of the phenyl cyclohexanol can be dehydrated to form phenylcyclohexene using a suitable acid catalyst; including both solid acid catalysts, such as zeolite beta, zeolite Y, zeolite X, ZSM-12, and mordenite and liquid acids, such as sulfuric acid. Dehydration conditions including a temperature of about 20° C. to about 200° C. and a pressure of about 100 kPa to about 2000 kPa.

The phenylcyclohexene can then be hydrogenated to produce further cyclohexylbenzene, for example in the presence of a catalyst comprising (i) a hydrogenation component; and (ii) a support. The hydrogenation component may comprise at least one metal component selected from Groups 6 to 10 of the Periodic Table of Elements, such as platinum, palladium and compounds and mixtures thereof. The hydrogenation component may be present in an amount between about 0.1 wt % and about 10 wt %, or about 0.2 wt % to about 0.5 wt %, or about 0.3 wt %, wherein the wt % is based upon total weight of the hydrogenation catalyst. The support may comprise one or more of aluminum oxide, silica, silicate, aluminosilicates, including but not limited to, zeolytes and MCM-41, carbon, and a carbon nanotube. Impurities may also be present in the support. For example, sodium salts such as sodium silicate can be present from anywhere from about 0.01 wt % to about 2 wt % based upon total weight of the hydrogenation catalyst.

The hydrogenation conditions may be any conditions suitable to cause the phenylcyclohexene to react with hydrogen. In various embodiments, the hydrogenation conditions comprise a pressure of about 0 kPa, g (kPa, gauge) to about 3450 kPa, g, or about 500 kPa, g to about 2000 kPa, g, or about 750 kPa, g to about 1500 kPa, g, or about 1000 kPa, g and a temperature of about 10° C. to about 100° C., or about 40° C. to about 80° C., or about 65° C.

The ratio of propylene oxide to phenol/cyclohexanone can be controlled by adjusting the amount of oxidation reaction effluent that goes through cleavage vs. epoxidation of propylene. The resultant process is thus flexible as far as equipment sizing allows it to be and enables the production of propylene oxide, phenol, and cyclohexanone with no other low-value by-products.

In various embodiments, the propylene oxide produced herein is used to make a polyether polyol, a polyurethane resin, and/or propylene glycol.

The following examples illustrate various methods of making epoxidation catalysts useful in the invention described herein.

EXAMPLE 1

Formation of an Amorphous Aluminophosphate Catalyst

A solution (A) containing 500 grams of water, 45 grams of concentrated phosphoric acid, and 75 grams of concentrated sulfuric acid was prepared. Another solution (B) was prepared containing 1600 grams of water and 300 grams of sodium aluminate. Solution A was added slowly to solution B with stirring. The pH was adjusted to 9 by the addition of 50% sulfuric acid solution. The gel was then placed in a polypropylene bottle and placed in a steambox (100° C.) for 48 hours. The product formed was recovered by filtration, washed with excess water, and stored as a filtercake. The filtercake is dried overnight at 100° C. Thereafter the filtercake is calcined at 540° C. for a total of 3 hours in flowing air and then allowed to cool. The calcined material was then subjected to a total of four 1N ammonium nitrate solution exchanges, where N is an abbreviation for normality or concentration of exchangeable cation/anion. For ammonium nitrate, 1N is equivalent to 1M (molar). One hundred grams of ammonium nitrate solution were used per 10 grams of material. The exchanged material was dried overnight at 100° C. Thereafter the dried material was calcined at 500° C. for a total of 3 hours in flowing air.

EXAMPLE 2

Formation of an Amorphous Cobalt Aluminophosphate Catalyst

A solution was prepared containing 500 grams of water, 45 grams of concentrated phosphoric acid, 117 grams of cobalt nitrate and 75 grams of concentrated sulfuric acid. Another solution was prepared containing 1600 grams of water and 300 grams of aluminum sulfate. These two solutions were combined with stirring. The molar ratio of the cobalt/aluminum/phosphorous was 1/8/1. The pH of the product was adjusted to 9 with the addition of 50% solution of sulfuric acid. The material was placed in a polypropylene bottle and put in a steam box (100° C.) for 48 hours. The material was then filtered and washed and dried at ~85° C. A portion of the material was air calcined to 540° C. for six hours. The elemental analyses and physical properties are provided in Table 1.

TABLE 1

| Element | Wt % |
| --- | --- |
| Co | 7.1 |
| Al | 25.3 |
| P | 3.4 |

A portion of the above material was treated with a 0.1N solution of ammonium nitrate (100 ml of 0.1N ammonium nitrate solution to 10 grams of calcined material). This treatment was done a total of four times with fresh solution. The material was then filtered and washed and dried at ~85° C. A portion of the material was air calcined to 540° C. for six hours. The surface area of this material was 310 m$^2$/g.

EXAMPLE 3

Formation of a Cobalt Zirconia Catalyst

Two hundred and fifty grams of ZrOCl$_2$.8H$_2$O and eighty-eight grams of Co(NO$_3$)$_2$.6H$_2$O were dissolved with stirring in 1.5 liters of distilled water. Another solution containing 130 grams of conc. NH$_4$OH and 1.6 liters of distill water was prepared. These two solutions were combined at the rate of 50 ml/min using a nozzle mixing. The pH of the final composite was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this catalyst was calcined to 500° C. in flowing air for 3 hours.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for co-producing phenol and propylene oxide, the process comprising:
(a) contacting a composition comprising at least 0.5 wt % cyclohexylbenzene based upon the total weight of the composition with an oxygen-containing compound under oxidation conditions to produce an oxidation reaction effluent comprising at least 0.5 wt % cyclohexylbenzene hydroperoxide based upon the total weight of the oxidation reaction effluent; and (b) reacting at least a portion of the cyclohexylbenzene hydroperoxide produced in (a) with propylene in the presence of an epoxidation catalyst under conditions effective to produce an epoxidation reaction effluent comprising phenylcyclohexanol and propylene oxide;

(c) separating at least a portion of the propylene oxide from the epoxidation reaction effluent to leave a phenylcyclohexanol-containing stream;

(d) dehydrating at least a portion of the phenylcyclohexanol in said phenylcyclohexanol-containing stream to phenylcyclohexene;

(e) hydrogenating at least a portion of the phenylcyclohexene from (d) to cyclohexylbenzene; and (f) recycling at least a portion of the cyclohexylbenzene from (e) to said contacting (a).

2. The process of claim 1, wherein the composition comprises at least 5 wt % cyclohexylbenzene based upon total weight of the composition and the oxidation reaction effluent comprises at least 5 wt % cyclohexylbenzene hydroperoxide, based upon total weight of the oxidation reaction effluent.

3. The process of claim 1, wherein said contacting in (a) is conducted in the presence of an oxidation catalyst comprising a cyclic imide.

4. The process of claim 3, wherein the cyclic imide is N-hydroxyphthalimide.

5. The process of claim 1, wherein said epoxidation catalyst comprises a metal and a support, said metal being selected from one or more of a Group 1 metal, a Group 2 metal, a Group 3 metal, a Group 8 transition metal, a Group 9 transition metal, a Group 10 transition metal, and mixtures thereof.

6. The process of claim 5, wherein said support comprises one or more of silica, alumina, crystalline or amorphous aluminophosphates, Group 4 metal oxides, mesoporous molecular sieves, and mixtures thereof.

7. The process of claim 1, wherein said epoxidation catalyst comprises cobalt on a support comprising at least one of zirconium oxide, an aluminophosphate, or a mixture thereof.

8. A process for co-producing phenol and propylene oxide, the process comprising:

(a) contacting cyclohexylbenzene with an oxygen-containing compound under oxidation conditions effective to produce an oxidation reaction effluent comprising cyclohexylbenzene hydroperoxide;

(b) reacting a first portion of the cyclohexylbenzene hydroperoxide produced in (a) with propylene in the presence of an epoxidation catalyst under conditions effective to produce an epoxidation reaction effluent comprising phenylcyclohexanol and propylene oxide; and (c) contacting a second portion of the cyclohexylbenzene hydroperoxide produced in (a) with a cleavage catalyst under conditions effective to convert said cyclohexylbenzene hydroperoxide into phenol and cyclohexanone;

(d) separating at least a portion of the propylene oxide from the epoxidation reaction effluent to leave a phenylcyclohexanol-containing stream;

(e) dehydrating at least a portion of the phenylcyclohexanol in said phenylcyclohexanol-containing stream to phenylcyclohexene;

(f) hydrogenating at least a portion of the phenylcyclohexene from (e) to cyclohexylbenzene; and (g) recycling the cyclohexylbenzene from (f) to said contacting (a).

9. The process of claim 8, wherein said contacting (a) is conducted in the presence of an oxidation catalyst comprising N-hydroxyphthalimide.

10. The process of claim 8, wherein said epoxidation catalyst comprises a metal and a support, said metal being selected from one or more of a Group 1 metal, a Group 2 metal, a Group 3 metal, a Group 8 transition metal, a Group 9 transition metal, a Group 10 transition metal, and mixtures thereof.

11. The process of claim 10, wherein said support comprises one or more of silica, alumina, crystalline or amorphous aluminophosphates, Group 4 metal oxides, mesoporous molecular sieves, and mixtures thereof.

12. The process of claim 8, wherein said epoxidation catalyst comprises cobalt on a support comprising zirconium oxide, an aluminophosphate, or a mixture thereof.

13. The process of claim 8, wherein said cleavage catalyst is an acid catalyst.

14. The process of claim 8, wherein said cleavage catalyst comprises sulfuric acid, an aluminosilicate zeolite, or a mixed metal oxide.

15. A process for co-producing phenol and propylene oxide, the process comprising:

(a) contacting benzene with hydrogen in the presence of a hydroalkylation catalyst under conditions effective to produce cyclohexylbenzene;

(b) contacting cyclohexylbenzene from (a) with an oxygen-containing compound under oxidation conditions effective to produce an oxidation reaction effluent comprising cyclohexylbenzene hydroperoxide;

(c) reacting a first portion of the cyclohexylbenzene hydroperoxide produced in (b) with propylene in the presence of an epoxidation catalyst under conditions effective to produce an epoxidation reaction effluent comprising phenylcyclohexanol and propylene oxide;

(d) contacting a second portion of the cyclohexylbenzene hydroperoxide produced in (b) with a cleavage catalyst under conditions effective to convert said cyclohexylbenzene hydroperoxide into phenol and cyclohexanone;

(e) separating at least a portion of the propylene oxide from the epoxidation reaction effluent to leave a phenylcyclohexanol-containing stream;

(f) dehydrating at least a portion of the phenylcyclohexanol in said phenylcyclohexanol-containing stream to phenylcyclohexene;

(g) hydrogenating at least a portion of the phenylcyclohexene from (f) to cyclohexylbenzene; and (h) recycling at least a portion of the cyclohexylbenzene from (g) to said contacting (a).

16. The process of claim 15, wherein said contacting (b) is conducted in the presence of N-hydroxyphthalimide.

17. The process of claim 15, wherein said epoxidation catalyst comprises a metal and a support, said metal being selected one or more of a Group 1 metal, a Group 2 metal, a Group 3 metal, a Group 8 transition metal, a Group 9 transition metal, a Group 10 transition metal, and mixtures thereof.

18. The process of claim 17, wherein said support comprises one or more of silica, alumina, crystalline or amorphous aluminophosphates, Group 4 metal oxides, mesoporous molecular sieves, and mixtures thereof.

19. The process of claim 15, wherein said epoxidation catalyst comprises cobalt on a support comprising zirconium oxide, an aluminophosphate, or a mixture thereof.

20. The process of claim 15, wherein said cleavage catalyst comprises sulfuric acid, an aluminosilicate zeolite, or a mixed metal oxide.

\* \* \* \* \*